US00RE34682E

United States Patent [19]

Vishnupad et al.

[11] E Patent Number: Re. 34,682

[45] Reissued Date of Patent: Aug. 2, 1994

[54] AQUEOUS DISPERSIONS OF POLYESTER AND POLYESTERAMIDES CROSS-LINKED WITH METALLIC IONS AND CASTS MADE THEREFROM

[75] Inventors: Mohan Vishnupad, Monroe; Jose Ramirez, Trumbull, both of Conn.

[73] Assignee: Imaginative Research Associates, Inc., Bridgeport, Conn.

[21] Appl. No.: 16,806

[22] Filed: Feb. 11, 1993

Related U.S. Patent Documents

Reissue of:

[64] Patent No.: 4,992,508
Issued: Feb. 21, 1991
Appl. No.: 367,183
Filed: Jun. 16, 1989

[51] Int. Cl.[5] ..... C08L 67/00

[52] U.S. Cl. ..... 524/601; 528/272; 528/275; 528/281; 528/282; 524/602; 524/605; 524/608; 524/755; 524/763; 524/764; 524/767; 524/783

[58] Field of Search ..... 528/272, 275, 281, 282; 524/601, 602, 605, 608, 755, 763, 764, 767, 783

[56] References Cited

U.S. PATENT DOCUMENTS

| | | | |
|---|---|---|---|
| 3,493,550 | 2/1970 | Schmitt et al. | 525/330.2 |
| 3,562,034 | 2/1971 | Edwards | 526/240 |
| 3,734,874 | 5/1973 | Kibler | 524/603 |
| 3,879,168 | 4/1975 | Franklin | 8/115.5 |
| 3,887,756 | 6/1975 | Gerstin et al. | 428/425 |
| 3,949,742 | 4/1976 | Nowakowski | 128/155 |
| 4,022,880 | 5/1977 | Vinson et al. | 424/49 |
| 4,100,269 | 7/1978 | Pader | 424/49 |
| 4,233,196 | 11/1980 | Sublett | 524/602 |
| 4,252,885 | 2/1981 | McGrail | 430/160 |
| 4,300,580 | 11/1981 | O'Neill | 132/7 |
| 4,304,900 | 12/1981 | O'Neil | 528/290 |
| 4,304,901 | 2/1981 | O'Neill | 528/290 |
| 4,335,220 | 6/1982 | Coney | 523/414 |
| 4,393,048 | 7/1983 | Mason | 424/122 |
| 4,409,285 | 10/1983 | Swerdlow | 428/332 |
| 4,478,907 | 10/1984 | Van Gossum | 428/327 |
| 4,502,976 | 3/1985 | Heller | 252/315.4 |
| 4,704,325 | 11/1987 | Crocker | 428/323 |
| 4,724,240 | 2/1988 | Abrutyn | 514/847 |
| 4,787,984 | 11/1988 | Hutchings | 210/698 |
| 4,849,213 | 7/1989 | Schaeffer | 424/53 |

FOREIGN PATENT DOCUMENTS

| | | |
|---|---|---|
| 0022624 | 1/1981 | European Pat. Off. . |
| 1545403 | 11/1967 | France . |
| 2211474 | 7/1974 | France . |

OTHER PUBLICATIONS

Eastman Publication No. J-257A dated May 1986 entitled "Preparation of Water-Resistant Coatings and Durable Binders Containing Eastman TM (WD3652) Water Dispersible Polymers".

"Eastman AQ TM Polymer-A Unique Dispersant For Hydrophobic Materials" by Michael J. Idacavage dated Dec. 1987.

*Primary Examiner*—Samuel A. Acquah
*Attorney, Agent, or Firm*—Dilworth & Barrese

[57] ABSTRACT

Cross-linked aqueous dispersions and emulsions and method for producing casts of any desirable shape therefrom the dispersions comprising a water dissipatable polymer in an amount from 18 to 30 percent by weight based on the total weight of the composition: water in an amount from [67 to 130] *30–80* percent by weight based on the total weight of the composition; a source of multivalent metallic ions in an amount of 0.1 to 5 percent by weight based on the total weight of the composition; and humectant in an amount from 0.1 to 40 percent by weight based on the total weight of the composition and the emulsions comprising a water dissipatable polymer in an amount from 18 to 30 percent by weight based on the total weight of the composition; water in an amount from [67] *30* to 80 percent by weight based on the total weight of the comosition; emollient oils in an amount from 0.1 to 25 percent by weight based on the total weight of the composition; a source of multivalent metallic ions in an amount from 0.1 to 5 percent by weight based on the total weight of the composition; humectants in an amount from 0.1 to 40 percent by weight based on the total weight of the composition; and emulsifier in an amount from 0.01 to 5 percent by weight based on the total weight of the composition.

3 Claims, No Drawings

AQUEOUS DISPERSIONS OF POLYESTER AND POLYESTERAMIDES CROSS-LINKED WITH METALLIC IONS AND CASTS MADE THEREFROM

Matter enclosed in heavy brackets [ ] appears in the original patent but forms no part of this reissue specification; matter printed in italics indicates the additions made by reissue.

FIELD OF THE INVENTION

This invention relates generally to cross-linking an aqueous dispersion of polyester or polyesteramide with the water soluble multivalent metallic ions. The aqueous dispersion of polyester or polyesteramides containing ether and sulfonate groups can also contain humectants and/or emollients which when cross-linked with metallic ions and poured into any desirable shaped mold form a clear or opaque cast of therapeutic functional nature. This invention also relates to the process of cross-linking the polyester or polyesteramide aqueous dispersion with metallic ions.

BACKGROUND OF THE INVENTION

Many compositions used for skin treatment contain emollients of humectants in lotion, cream or gel form. Such products are applied by evenly spreading the product on the skin. Upon loss of water, the product dries providing humectants and emollients to the epidermis.

Water soluble gels that form protective films of various types are known. For example, U.S. Pat. No. 4,393,048 discloses a water soluble hydrogel of alkali metal alginate and glycerine that dries to a non-toxic, pliable protective film. U.S. Pat. No. 3,949,742 discloses a transparent medical dressing which performs as a synthetic film over skin wounds. Water soluble polyesters, for example U.S. Pat. No. 4,502,976, are used to form cross-linked bioerodible hydrogels. The hydrogels, suitable for carrying water soluble therapeutic macromolecules and for implantantion in living mammals, are produced by a complex polymerization process without using water soluble metallic ions.

U.S. Pat. No. 3,879,168 to Franklin discloses a surgical dressing made of partially soluble alginic materials in the form of gauze or wool characterized by a pH of 4 to 7 and a calcium content of 2–6% by weight comprised of a laminate of a thin layer of non-porous segmented polyurethane sewn to foam.

U.S. Pat. Nos. 3,734,874, 4,233,196, 4,335,220, 4,304,900, 4,304,901, and 4,300,580 describe water-dissipatable, meltable polyesters that are useful as adhesives, coating materials, films, packaging materials and other products that can be dissolved, dispersed or otherwise dissipated in water or aqueous solutions. These polyesters, however, are not cross-linked using metallic ions and cast into shapes to entrap water, humectants and/or emollients within the hardened cast.

As explained in a technical publication from Eastman, the water dispersability of the AQ polymer is largely attributed to the presence of ionic substituents attached to the polymer chain. A simplified representation of the polymer is shown below:

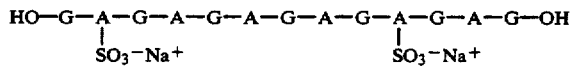

wherein "A" is an aromatic dicarboxylic acid moiety some of which have sodiofulfo (—$SO_3$−, Na+) substituents, "G" is an aliphatic or cycloaliphatic glycol residue and "OH" is a hydroxy end group.

It is the sodio sulfo group which impart the water dispersability to the polymer. To cross-link with multivalent metallic ions and obtain the moldable shapes of this invention, the multivalent metal salts must be added and mixed according to the teaching of this invention. Departing from this process results in non-compatible mixtures of non-commercial properties. Eastman technical publications teach the synthesis and preferred methods for crosslinking water dispersible polyesters and polyesteramides with other resins through high temperature curing process and subsequent drying of the cured resins, but specifically warn against the use of the heavy metal salts included in this invention as being not compatable with the polymers used in this invention.

OBJECTS OF THE INVENTION

It is therefore an object of the present invention to provide novel cross-linked polyester polymers with humectants and/or emollients by using water soluble metallic ions.

A further object of the present invention is to provide a convenient process of cross-linking the humectant and emollients with the polyester polymer in the presence of water soluble metallic ions.

A further object of this invention is to provide such casted patches containing water soluble medicaments and oil soluble medicaments. Such patches can be used as controlled release transdermal delivery patches.

SUMMARY OF THE INVENTION

It has been found that the objectives of this invention may be realized by forming a cast containing humectants and/or emollient oils, water, water dissipatable polyesters, and by cross-linking with water soluble multivalent metal ions. Such compositions when poured into a mold harden without pressure and have utility in wound treatment, skin treatment and controlled release drug and fragrance patches.

The casts of this invention comprise water dissipatable polyester or polyesteramide in an amount from 18 to 30 percent by weight, water in an amount from [67] *30* to 80%, humectants in an amount from 0.01 to 40% by weight, and a source of multivalent metal ions for cross-linking purposes in an amount from 0.01 to 5 percent. Casts of this invention can also be formulated using emollient oils in an amount from 0.01 to 25% by weight based on the total weight of the composition, water dissipatable polyester in an amount from 18–30% by weight, water in an amount from [67]*30*–80% by weight based on the total weight of the composition, and a source of multivalent metallic ions in an amount from 0.01 to 5% based on the total weight of the composition. Optionally the composition also contains fragrance oils, medical agents or color.

DETAILED DESCRIPTION OF THE INVENTION

Cross-linked clear casts of the present invention comprise (a) a water dissipatable polyester polymer in an amount from 18–30% by weight based on the total weight of the composition; (b) water in an amount from [67]*30*–80% by weight based on the total weight of the composition; (c) a source of multivalent metallic ions in an amount of 0.1–5% by weight based on the total weight of the composition; (d) humectant such propylene glycol, glycerine in an amount from 0.1–40% by weight based on the total weight of the composition.

The cross-linked cast of the present invention can also be in the form of an opaque emulsion system. Such emulsion cast of the present invention comprise (a) a water dissipatable polymer in an amount from 18 to 30% by weight based on the total weight of the composition; (b) water in an amount from [67]*30* to 80% by weight based on the total weight of the composition; (c) emollient oils in an amount from 0.1 to 25% by weight based on the total weight of the composition; (d) a source of multivalent metallic ions in an amount from 0.1 to 5% by weight based on the total weight of the composition; (e) humectants in an amount from 0.01 to 40% by weight-based on the total weight of the composition; (f) any suitable oil-in-water emulsifier in an amount from 0.01 to 5% by weight based on the total weight of the composition.

Polymers useful in the present invention must be capable of cross-linking with water soluble metal ions, and, when poured in liquid from into a mold hardening without pressure to form a cast of any desirable shape. Polymers suitable for use in this invention include the water-dissipatable polyester and polyesteramides described in U.S. Pat. No. 3,734,874 to Kibler, et al., U.S. Pat. No. 4,233,196 to Sublet and U.S. Pat. No. 4,304,901 to O'Neill, et al. A preferred water dissipatable polyester is commercially available on Eastman AQ 55S polymers.

Examples of organic and inorganic sources of the multivalent metal ions used to cross-link the polymers in this invention include magnesium chloride, zinc acetate, zinc gluconate, zinc oxide, titanium dioxide, and magnesium acetate. The preferred sources of multivalent metal ions are water soluble and include zinc gluconate and magnesium chloride.

In forming the clear cross-linked casts of this invention, water by itself or in combination with humectant such as propylene glycol and glycerine may be used.

In forming cross-linked emulsion casts of this invention any emollient oil may be used. Emollients useful in this invention include hydrocarbon oils and semi-solid hydrocarbons, lanolin and derivatives, silicone oils and esters commonly used in the cosmetic and dermatological fields.

The cross-linking of polymer containing emulsion systems by means of multivalent metallic ions can be achieved with or without the additional emulsfiers. The selection of an appropriate emulsifier for a given system is within the purview of one skilled in the art.

Optionally, a wide variety of agents may be incorporated into the compositions of this invention for a variety of purposes. For example, medicaments such as benzoyl peroxide, methyl nicolinate, salicylic acid, benzocaine and methanol can be cast into desirable shapes for therapeutic use.

The cross-linked hydrogels and emulsions can be cast into any desirable shape and used for various purposes. For example, casts in the form of face masks may be used for treating dry skin. Casts in the form of patches or pads may be used to cover burns and wounds for soothing and comforting the inflamed area, or for delivering active medicaments to the damaged skin as a controlled release, transdermal patch.

Both the clear and opaque emollient casts may also contain fragrance, insect repellents, sun screens and like chemicals.

The following examples illustrate how the cross-linked casts of this invention may be formed.

EXAMPLE 1

A clear cross-linked cast was produced having the following composition:

| | |
|---|---|
| Eastman AQ 55S Polymer | 24.0 |
| Zinc Gluconate (USP) | 2.0 |
| Propylene Glycol | 34.0 |
| Water | [42.0] *40* |

The cross-linked cast of Example 1 was prepared by placing the appropriate amounts of water and propylene glycol into a suitable container and heating the mixture to 80° C. The appropriate amount of polymer was gradually added with a high shear mixing to dissolve the solids. When all the solids were added, high shear mixing is continued, until a clear, straw colored, thick gel was produced. The gel was then cooled to room temperature and an appropriate amount of zinc gluconate aqueous solution added by high shear mixture until cross-linking occurred. The liquid was poured into a mold of desirable shape to produce a cast of hydrogel. The metallic cross-linking can be done either at room temperature or at elevated temperatures depending on the composition.

EXAMPLE 2

An emulsion crosslinked cast was produced having the following composition:

| | |
|---|---|
| Eastman AQ 55S Polymer | 20.3 |
| Propylene Glycol | 28.0 |
| Mineral oil | 10.0 |
| PJ | 7.0 |
| Polysorbate 20 | 1.0 |
| Zinc gluconate | 2.0 |
| Water | 31.7 |

The cross-linked emulsion casts of Example 2 were formed by placing appropriate amounts of water and propylene glycol in a suitable container and heating the mixture to 80° C. The appropriate amount of polymer was gradually added with a high shear mixing until a clear viscous liquid was produced. The polysorbate 20 was added to the clear liquid and mixing continued. The melted oil phase was then added to the aqueous phase and homogenized to form a smooth emulsion. To this emulsion the appropriate amount of aqueous solution of znc gluconate was added with continued mixing. Pouring into a mold at appropriate viscosity formed a cast of the desired shape. The cross-linking of the emulsion can be carried out between 50° C., to 70° C., as desired, for manufacturing and suitable for pouring into the molds for casting purposes.

EXAMPLE 3

Water insoluble sources of multivalent metallic ions such as, for example, zinc oxide or titanium dioxide can be added to form more rigid cross-linked casts.

| | |
|---|---|
| Eastman AQ55S Polymer | 21.00 |
| Propylene Glycol | 28.00 |
| Petroleum Jelly | 15.00 |
| Glycerol Monostearate and Polyoxyethylene stearate | 1.00 |
| Zinc Oxide | 2.00 |
| Zinc Gluconate | 2.00 |
| Microcrystalline Wax | 5.00 |
| Water | 26.00 |

EXAMPLES 4–24

The following are additional specific examples of formulations used to produce cross-linked casts of this invention:

| | |
|---|---|
| Ex. 4 | |
| Eastman AQ 55S polymer | 21 |
| Propylene glycol | 28 |
| Zinc gluconate | 2 |
| Water | 49 |
| Ex. 5 | |
| Eastman AQ 55S polymer | 25.5 |
| Propylene glycol | 34.0 |
| Zinc gluconate | 2.0 |
| Water | 38.5 |
| Ex. 6 | |
| Eastman AQ 55S polymer | 20.3 |
| Propylene glycol | 18.0 |
| Zinc gluconate | 2.0 |
| Water | 59.7 |
| Ex. 7 | |
| Eastman AQ 55S polymer | 23.2 |
| Propylene glycol | 10.0 |
| Zinc gluconate | 2.0 |
| Water | 64.8 |
| Ex. 8 | |
| Eastman AQ 55S polymer | 21 |
| Propylene glycol | 28 |
| Zinc gluconate | 2 |
| Water | 49 |
| Ex. 9 | |
| Eastman AQ 55S polymer | 24 |
| Propylene glycol | 32 |
| Zinc gluconate | 2 |
| Water | 42 |
| Ex. 10 | |
| Eastman AQ 55S polymer | 27 |
| Propylene glycol | 36 |
| Zinc gluconate | 2 |
| Water | 35 |
| Ex. 11 | |
| Eastman AQ 55S polymer | 23.2 |
| Zinc gluconate | 2.0 |
| Water | 74.8 |
| Ex. 12 | |
| Eastman AQ 55S polymer | 23.2 |
| Magnesium chloride | 0.5 |
| Water | 76.3 |
| Ex. 13 | |
| Eastman AQ 55S polymer | 24 |
| Glycerine | 32 |
| Zinc gluconate | 2 |
| Water | 42 |
| Ex. 14 | |
| Eastman AQ 55S polymer | 24.0 |
| Propylene glycol | 32.0 |
| Magnesium chloride | 0.3 |
| Water | 43.7 |
| Ex. 15 | |

-continued

| | |
|---|---|
| Eastman AQ 29S polymer | 15.0 |
| Eastman AQ 55S polymer | 5.4 |
| Propylene glycol | 27.2 |
| Mineral oil | 10.0 |
| Polysorbate 20 | 2.0 |
| Zinc gluconate | 3.0 |
| Water | 37.4 |
| Ex. 16 | |
| Eastman AQ 55S polymer | 20.3 |
| Propylene glycol | 28.0 |
| Mineral oil | 10.0 |
| Petroleum jelly | 7.0 |
| Polysorbate 20 | 1.0 |
| Zinc gluconate | 2.0 |
| Water | 31.7 |
| Ex. 17 | |
| Eastman AQ 55S polymer | 20.3 |
| Propylene glycol | 28.0 |
| Mineral oil | 10.0 |
| Petroleum jelly | 7.0 |
| Polysorbate 20 | 1.0 |
| Zinc gluconate | 1.5 |
| Water | 32.2 |
| Ex. 18 | |
| Eastman AQ 55S polymer | 18.0 |
| Propylene glycol | 24.0 |
| Petroleum jelly | 17.0 |
| Polysorbate 20 | 1.0 |
| Zinc gluconate | 2.0 |
| Water | 38.0 |
| Ex. 19 | |
| Eastman AQ 55S polymer | 21 |
| Propylene glycol | 28 |
| Dimethicone | [19] *9* |
| Petroleum jelly | 9 |
| Glycerolmonostearate and Polyoxyethylene Stearate | 1 |
| Zinc gluconate | 2 |
| Water | 30 |
| Ex. 20 | |
| Eastman AQ 55S polymer | 21.0 |
| Propylene glycol | 28.0 |
| Petroleum jelly | 17.0 |
| Zinc gluconate | 2.0 |
| Water | 32.0 |
| Ex. 21 | |
| Eastman AQ 55S polymer | 21.0 |
| Propylene glycol | 28.0 |
| Petroleum jelly | 16.0 |
| Salicylic acid | 2.0 |
| Zinc gluconate | 2.0 |
| Water | [10.0] *31.0* |
| Ex. 22 | |
| Eastman AQ 55S polymer | 20.7 |
| Propylene glycol | 27.6 |
| Petroleum jelly | 15.0 |
| Benzoyl peroxide | 2.0 |
| Glycerine | 2.0 |
| Zinc gluconate | 2.0 |
| Water | 30.7 |
| Ex. 23 | |
| Eastman AQ 55S polymer | 21.0 |
| Propylene glycol | 28.0 |
| Menthol | 2.0 |
| Zinc gluconate | 2.0 |
| Water | [26.0] *47.0* |
| Ex. 24 | |
| Eastman AQ 55S polymer | 21.0 |
| Propylene glycol | 28.0 |
| Petroleum jelly | 15.0 |
| Polysorbate 20 | 1.0 |
| Superabsorbant polymer | 1.0 |
| Zinc gluconate | 1.0 |
| Water | 33.0 |

Although particular illustrative embodiments of the present invention have been described herein, the present invention is not limited to these particular embodiments. Various changes and modifications may be made thereto by those skilled in the art without departing from the spirit or scope of the invention, which is defined in the appended claims.

What is claimed is:

1. A cross linked aqueous dispersion composition comprising:

a water dissipatable polymer in an amount from 18 to 30 percent by weight based on the total weight of the compositions;

water in an amount from [67] *30* to 80 by weight based on the total weight of the composition;

a source of multivalent metallic ions in an amount of 0.1 to 5 percent by weight on the total weight of the composition; and humectant in an amount from 0.1 to 40 percent by weight based on the total weight of the composition.

2. A cross-linked dispersion composition according to claim 1 wherein said source of multivalent metallic ions is selected from the group consisting of magnesium chloride, zinc acetate, zinc gluconate, zinc oxide, titanium dioxide and magnesium acetate.

3. An article manufactured using the composition of claim 1.

* * * * *